United States Patent
Hamacher et al.

(10) Patent No.: US 11,491,332 B2
(45) Date of Patent: *Nov. 8, 2022

(54) COCHLEAR IMPLANT SYSTEM AND METHOD FOR DETECTING ELECTRODE MIGRATION USING ELECTRICALLY EVOKED COMPOUND ACTION POTENTIALS

(71) Applicant: ADVANCED BIONICS AG, Staefa (CH)

(72) Inventors: Volkmar Hamacher, Hannover (DE); Patrick J. Boyle, Kent (GB)

(73) Assignee: Advanced Bionics AG, Staefa (CH)

( * ) Notice: Subject to any disclaimer, the term of this patent is extended or adjusted under 35 U.S.C. 154(b) by 203 days.

This patent is subject to a terminal disclaimer.

(21) Appl. No.: 16/922,704

(22) Filed: Jul. 7, 2020

(65) Prior Publication Data

US 2020/0330763 A1   Oct. 22, 2020

Related U.S. Application Data

(63) Continuation of application No. 15/752,806, filed as application No. PCT/EP2015/068919 on Aug. 18, 2015, now Pat. No. 10,744,323.

(51) Int. Cl.
*A61N 1/36* (2006.01)
*A61N 1/375* (2006.01)
*A61N 1/05* (2006.01)

(52) U.S. Cl.
CPC ....... *A61N 1/36038* (2017.08); *A61N 1/0541* (2013.01); *A61N 1/36036* (2017.08); *A61N 1/375* (2013.01)

(58) Field of Classification Search
None
See application file for complete search history.

(56) References Cited

U.S. PATENT DOCUMENTS

| | | |
|---|---|---|
| 8,527,058 B2 | 9/2013 | Kulkarni et al. |
| 9,950,171 B2 | 4/2018 | Johanek |
| (Continued) | | |

FOREIGN PATENT DOCUMENTS

| | | |
|---|---|---|
| EP | 1972359 | 9/2008 |

OTHER PUBLICATIONS

International Search Report received in PCT Patent Application No. PCT/EP2015/068919, dated Nov. 28, 2017.

(Continued)

*Primary Examiner* — Kennedy Schaetzle
(74) *Attorney, Agent, or Firm* — ALG Intellectual Property, LLC

(57) ABSTRACT

A system includes a unit for capturing ECAP signals induced at electrodes of an electrode array in response to stimulation of a cochlea by applying auditory nerve stimulation signals to the electrodes; a memory unit for storing the captured ECAP signals and/or ECAP data derived from the captured ECAP signals; an electrode migration detection unit for detecting electrode migration relative to the cochlea by comparing presently captured ECAP signals and/or ECAP data derived from such presently captured ECAP signals to stored previously captured ECAP signals and/or ECAP data derived from such previously captured ECAP signals; and a unit for outputting an alarm signal in case that electrode migration is detected by the electrode migration detection unit.

20 Claims, 4 Drawing Sheets

(56) References Cited

U.S. PATENT DOCUMENTS

| | | |
|---|---|---|
| 10,744,323 B2 * | 8/2020 | Hamacher .......... A61N 1/36036 |
| 2005/0065427 A1 | 3/2005 | Magill |
| 2005/0261748 A1 | 11/2005 | Van Dijk |
| 2006/0235332 A1 | 10/2006 | Smoorenburg |
| 2006/0287690 A1 | 12/2006 | Bouchataoui et al. |
| 2008/0221640 A1 | 9/2008 | Overstreet et al. |
| 2010/0268302 A1 | 10/2010 | Botros |
| 2011/0245891 A1 | 10/2011 | Fritsch et al. |
| 2013/0274827 A1 | 10/2013 | Smoorenburg |
| 2014/0277282 A1 | 9/2014 | Jaax |
| 2015/0032181 A1 | 1/2015 | Baynham et al. |
| 2017/0173332 A1 | 6/2017 | Overstreet |

OTHER PUBLICATIONS

Non-Final Office Action received in U.S. Appl. No. 15/752,806 dated Oct. 1, 2019.

Dietz, et al., Electrode migration after cochlear implant surgery: more common than expected, Eur Arch Otorhinolaryngol. 2015; DOI 10.1007/s00405-015-3716-4.

Gaertner, et al., Electrodenmigration bei Cochlea-Implantat-Patienten: Moglichkeiten de Verdachtdiagnose wahrend der Nachsorge, 85th Annual Meeting of the German Society of Oto-Rhino-Laryngology, Head and Neck Surgery, May 28, 2014 to Jun. 1, 2014.

Van Der Marel, et al., Electrode Migration in Cochlear Implant Patients: Not an Exception, Audiol. Neurotol. 2012; 17(5), pp. 275 to 281.

* cited by examiner

COCHLEAR IMPLANT SYSTEM AND METHOD FOR DETECTING ELECTRODE MIGRATION USING ELECTRICALLY EVOKED COMPOUND ACTION POTENTIALS

RELATED APPLICATIONS

The present application is a continuation of U.S. patent application Ser. No. 15/752,806 filed Feb. 14, 2018, which application claims priority to International Application No. PCT/EP2015/068919, filed Aug. 18, 2015, the contents of which are hereby incorporated by reference in their entirety.

BACKGROUND INFORMATION

The invention relates to a cochlear implant system comprising a microphone arrangement, a sound processor and an implantable stimulation assembly comprising an electrode array to be implanted in the cochlea of a patient.

Proper operation of a cochlear implant (CI) system requires that the electrode array, after implantation in the cochlea by surgery, remains in the desired position relative to the cochlea, so that each electrode may stimulate the cochlea at the desired stimulation site. Ideally, the position of each electrode remains constant after implantation.

However, migration (or backing-out or extrusion) of electrodes may happen after implantation for various reasons: there may be tension of the electrode array inside the cochlea, especially for straight electrode array designs, there may be a spring effect on the electrode lead, the skull may grow (in particular in case that the patient is a child), or a sheath may grow around an electrode, pushing the electrode out, etc. Typically, such post-operative electrode array migration is outward, but in some cases also an inward migration has been observed. The amount of migration typically is in the range of 1 to 5 electrode contacts. There are some indications that the occurrence of electrode migration has increased since thin and relatively short lateral wall electrode array designs had become available which do not sit as "tightly" in the scala tympani as earlier electrode arrays of larger diameter.

While surgeons try to mitigate the risk of electrode migration by proper fixation of the electrode lead, electrode migration nevertheless may occur even months or years after surgery. Typically, electrode migration is detected by post-operative imaging made in response to complaints by the patient caused by sudden degradation of sound quality and/or speech understanding. Such imaging requires sedation of the pediatric patient and radiologic investigation.

Electrode migration is particularly problematic in cases in which the patient is a baby or young child who cannot report changes in sound perception, so that an electrode migration may remain undiscovered until delayed speech acquisition or other auditory deficiencies are observed.

Upon detection of electrode migration, the patient may be re-fitted, electrode contacts believed to be outside the cochlea may be switched off, or a revision surgery may be performed.

Studies on the likelihood and detection of electrode migration in CI patients is found in the articles "Electrode Migration in Cochlear Implant Patients: Not an Exception" by K. S. van der Marel et al., Audiol. Neurotol. 2012; 17(5), pages 275 to 281 and "Electrode migration after cochlear implant surgery: more common than expected" by A. Dietz et al., Eur Arch Otorhinolaryngol. 2015; DOI 10.1007/s00405-015-3716-4.

U.S. Pat. No. 8,527,058 B2 relates to a CI system which is able to measure the impedance of the electrodes in order to automatically adjust signal processing parameters to the presently measured electrode impedance and/or to output an alert to the patient, such as a visual alert via a LED or a graphical interface, an audible beep or a text message in order to make the patient or other person aware that the patient may need to visit a clinician to readjust the stimulation parameters according to the impedance changes.

A standard tool for evaluating the performance of an implanted CI device for fitting purposes is the use of electrically evoked compound action potentials ("ECAP") which can be recorded using the intra-cochlear electrodes and sent back to the external processor of the CI system by back-telemetry. The ECAPs are recorded in response to electrical stimulation of the cochlea via at least one of the implanted electrodes in order to assess the basic functioning of the electrodes and the integrity of the electrode-nerve interface. The ECAP is a voltage signal which comprises a negative and a smaller positive peak; the typical order of magnitude of the ECAP is between 1 and 1000 µV. To a first approximation, the ECAP magnitude is monotonically related to the amount of auditory nerve fibers that respond to the electrical stimulus. In particular, an ECAP may be used for determining the neural response threshold of each electrode (i.e. the minimal electrode current that generates a measurable ECAP, or the minimum interpulse interval at a given stimulation current which generates a measurable ECAP) which may be determined from a linear fit of a so-called growth function measurement. An example of such ECAP measurements during surgery for first fitting of the CI system is described in US 2008/0221640 A1. An example of the measurement of ECAPs for determining the perception threshold during a fitting session is described in US 2015/0032181 A1.

Further, it is reported in the presentation "Electrodenmigration bei Cochlea-Implantat-Patienten: Moglichkeiten der Verdachtsdiagnose während der Nachsorge", by Gaertner et al., 85th Annual Meeting of the German Society of Oto-Rhino-Laryngology, Head and Neck Surgery, May 28 to Jun. 1, 2014, in Dortmund, that electrode migration may lead to an electrode-wise shift of ECAP thresholds of the electrodes.

It is an object of the invention to provide for a CI system which allows for an early and convenient detection of post-operative electrode array migration; in particular, such system should be suitable also for young children.

According to the invention, this object is achieved by a CI system as defined in claim 1 and a corresponding method of operating such CI system as defined in claim 17, respectively.

The invention is beneficial in that, by providing the cochlear implant system with an electrode migration monitoring unit which regularly captures ECAP signals induced at the electrodes and compares the captured ECAP signals and/or ECAP data, such as the ECAP threshold, derived from the captured ECAP signals with stored previously captured ECAP signals or derived ECAP data in order to detect electrode migration and to output a corresponding alarm signal in case that electrode migration is detected, electrode migration can be almost immediately recognized without treatment, such as sedation and radiologic investigation, of the patient and without any specific cooperation of the patient, such as giving specific perceptual feedback or visiting a clinician, being required.

Preferred embodiments of the invention are defined in the dependent claims.

BRIEF DESCRIPTION OF THE DRAWINGS

Hereinafter examples of the invention will be illustrated by reference to the attached drawings, wherein.

DETAILED DESCRIPTION

Figure 1:
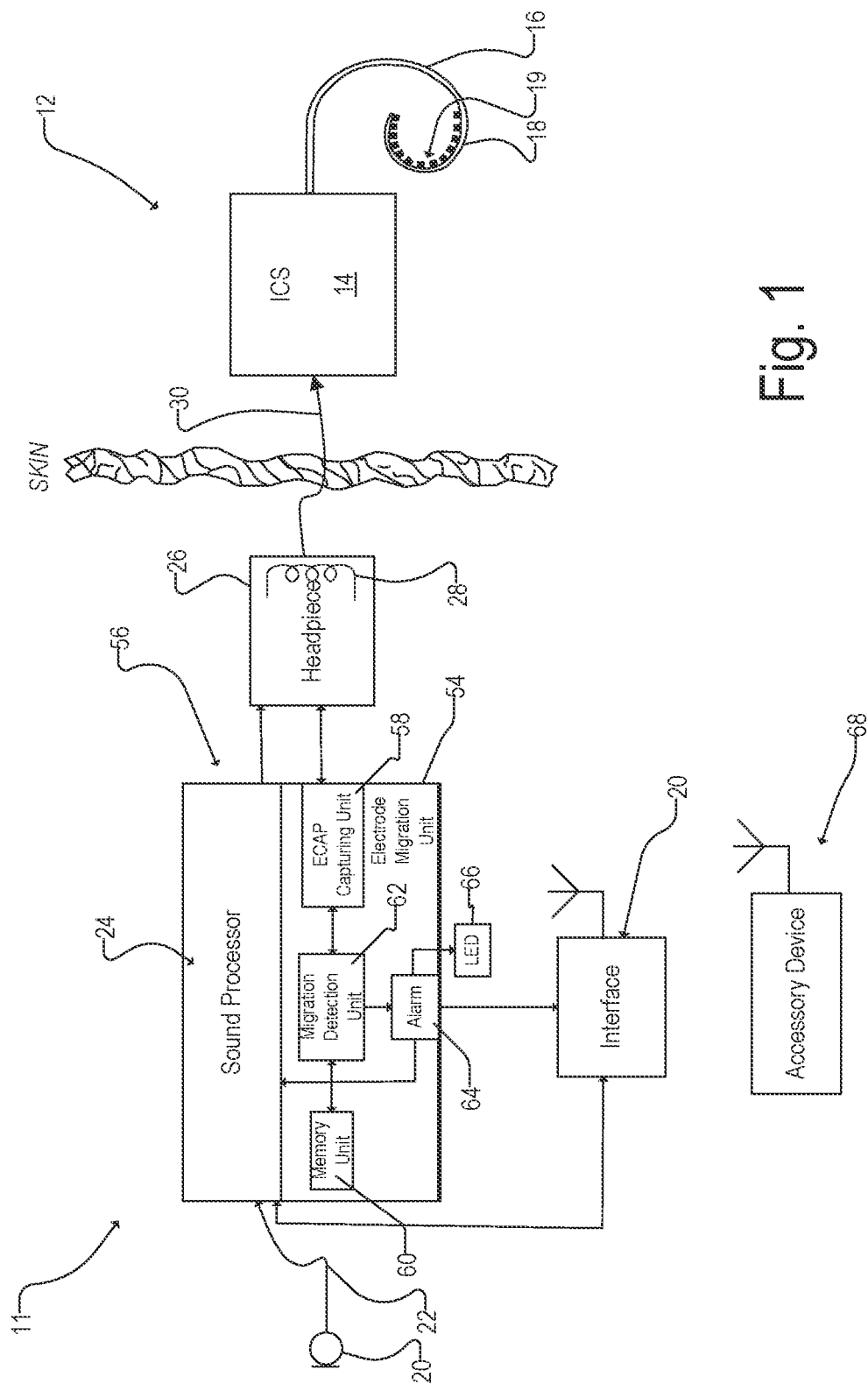
FIG. 1 is a schematic representation of an example of a CI system according to the invention.

In FIG. 1 an example of a cochlear implant system is shown schematically. The system comprises a sound processing sub-system 11 and a stimulation sub-system 12. The sound processing sub-system 11 serves to detect or sense an audio signal and divide the audio signal into a plurality of analysis channels each containing a frequency domain signal (or simply "signal") representative of a distinct frequency portion of the captured audio. A signal level value is determined for each analysis channel by analyzing the respective frequency domain signal. Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient in accordance with the stimulation parameters received from the sound processing sub-system 11. Electrical stimulation is provided to the patient 17 via a CI stimulation assembly ("electrode array") 19 comprising a plurality of stimulation channels, wherein various known stimulation strategies, such as current steering stimulation or N-of-M stimulation, may be utilized. In addition, the stimulation assembly 19 also is used for ECAP measurements via reverse telemetry, as will be described in more detail with regard to FIG. 4 below.

Figure 2:
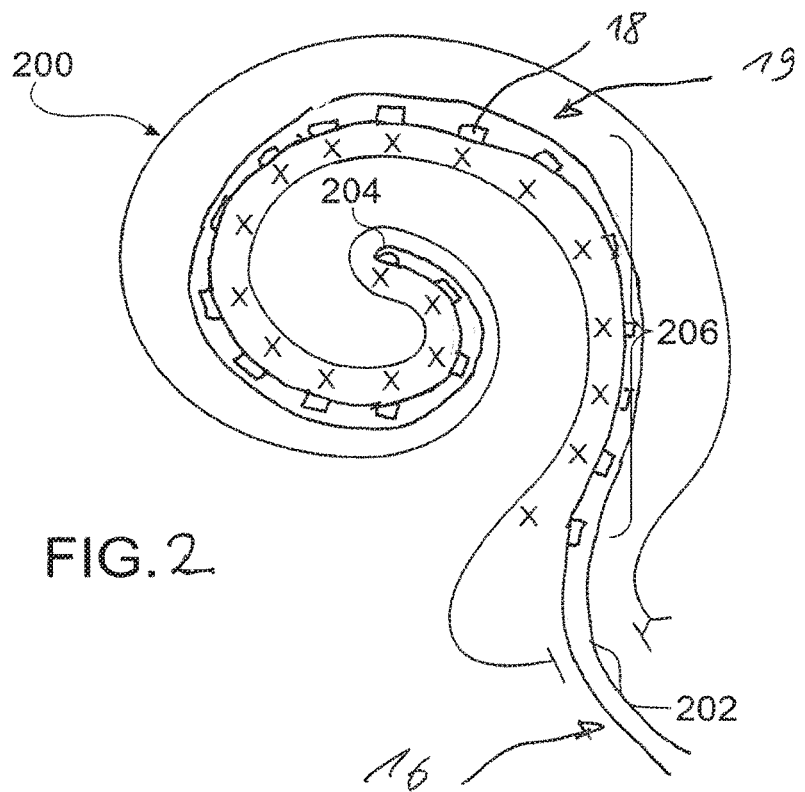
FIG. 2 is a cross-sectional view of a human cochlea with marked stimulation sites and an implanted electrode array.

FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 (FIG. 1) is configured to apply stimulation to different locations within the cochlea 200 (e.g., different locations along the auditory nerve tissue 206) to provide a sensation of hearing (in the schematic illustration of FIG. 2 each of the electrodes 18 of the electrode array 19 is attributed to a different one of the stimulation sites by positioning the electrode array in an appropriate manner within the cochlea 200, so that each electrode contact is located at the desired stimulation site).

Returning to FIG. 1, sound processing subsystem 11 and stimulation subsystem 12 are configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 1, the stimulation sub-system 12 comprises an implantable cochlear stimulator ("ICS") 14, a lead 16 and the stimulation assembly 19 disposed on the lead 16. The stimulation assembly 19 comprises a plurality of stimulation contacts ("electrodes") 18 for electrical stimulation of the auditory nerve. The lead 16 may be inserted within a duct of the cochlea in such a manner that the stimulation contacts 18 are in communication with one or more stimulation sites within the cochlea, i.e. the stimulation contacts 18 are adjacent to, in the general vicinity of, in close proximity to, directly next to, or directly on the respective stimulation site.

In the example shown in FIG. 1, the sound processing sub-system 11 is designed as being located external to the patient 17; however, in alternative examples, at least one of the components of the sub-system 11 may be implantable.

In the example shown in FIG. 1, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 3:
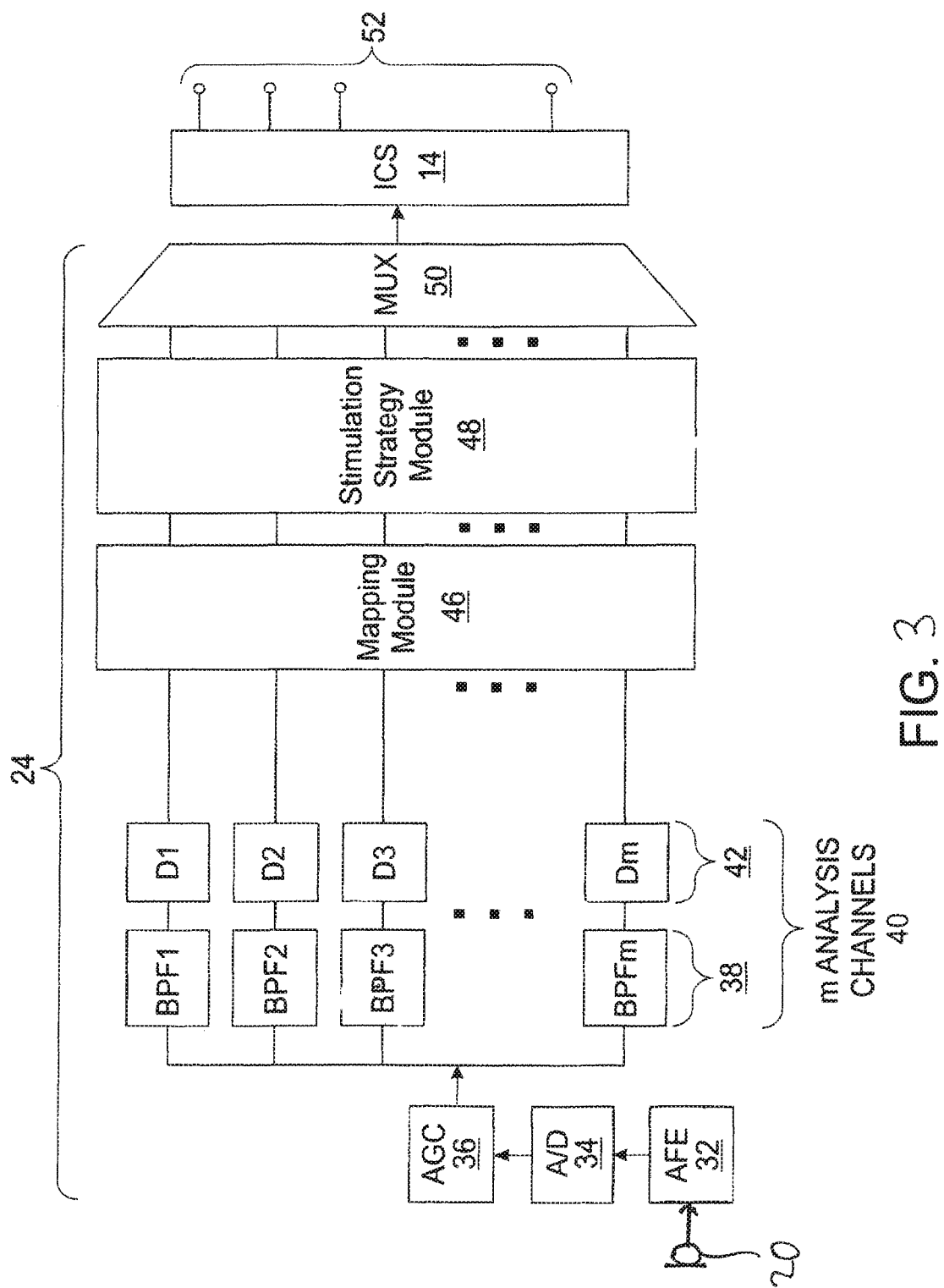
FIG. 3 is a block diagram of an example of the signal processing structure of a CI system according to the invention.

In FIG. 3 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then dividing the resulting frequency bins into the analysis channels 40.

The signals within each analysis channel 40 are input into an envelope detector 42 in order to determine the amount of energy contained within each of the signals within the analysis channels 40. The output signals of the envelope detectors 42 are supplied to a mapping module 46 which serves to map the signals in the analysis channels 40 to the stimulation channels 52. For example, signal levels may be mapped to amplitude values used to define the electrical stimulation pulses that are applied to the patient by the ICS 14 via M stimulation channels 52. For example, each of the n stimulation channels 52 may be associated to one of the stimulation contacts 18 or to a group of the stimulation contacts 18.

The sound processor 24 further comprises a stimulation strategy module 48 which serves to generate one or more stimulation parameters based on the signals in the analysis channels 40 and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels in order to effectuate a current steering stimulation strategy. Additionally or alternatively, the stimulation strategy module 48 may be configured to generate stimulation parameters which direct the ICS 14 to apply electrical stimulation via only a subset N of the stimulation channels 52 in order to effectuate an "N-of-M" stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit (not shown). Such control parameters may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values and/or filter characteristics. Examples of such auditory prosthesis devices, as described so far, can be found, for example, in WO 2011/032021 A1.

Figure 4:
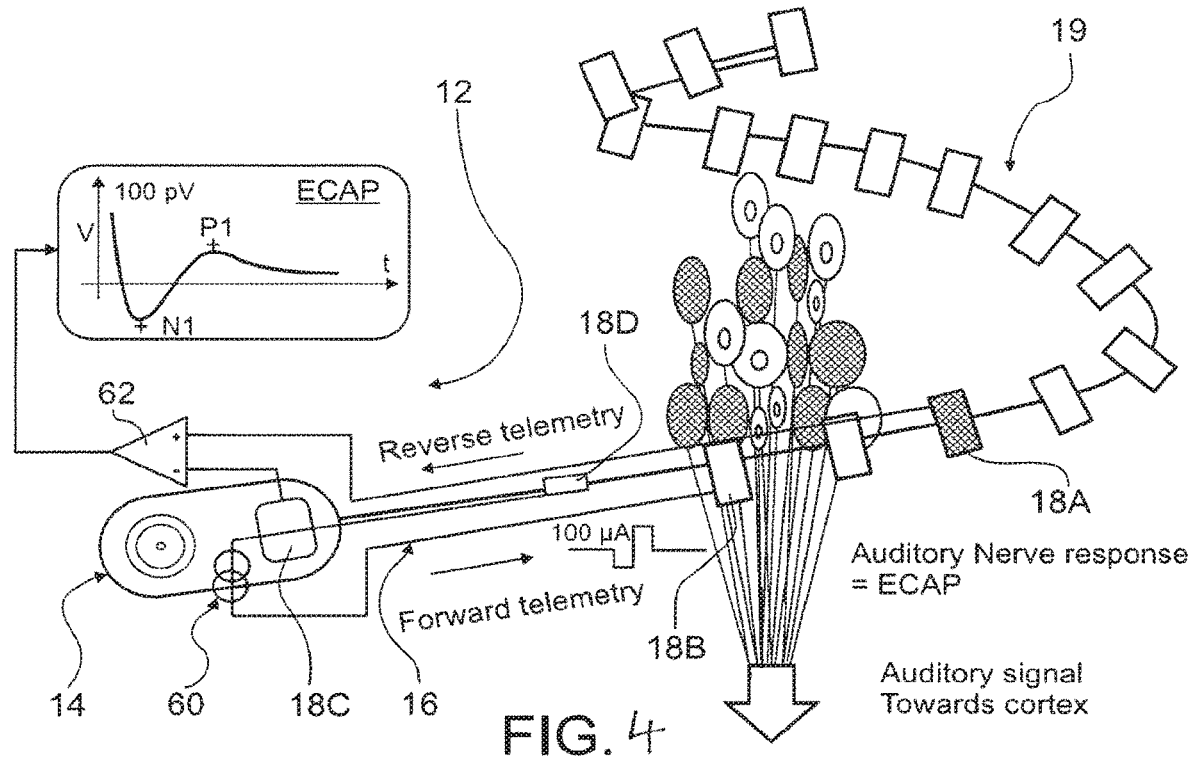
FIG. 4 is a schematic illustration of a setup for ECAP measurements by reverse telemetry.

FIG. 4 shows a schematic illustration of an example of auditory nerve excitation and the resulting ECAP recording at electrode 18A by reverse telemetry, following electrical stimulation at electrode 18B by forward telemetry (the stimulated neurons are indicated by dark grey circles in FIG. 4, the return electrodes for electrical stimulation and ECAP measurement are indicated at 18C and 18D, respectively). The current-source 60 and the amplifiers 62 are positioned inside the receiver part of the ICS 14. The typical ECAP peaks are indicated at N1 and P1 in example of an ECAP signal vs. time in FIG. 4. The peaks may be used as markers to measure the ECAP amplitude as the differential voltage between P1 and N1.

Examples of ECAPs measurements which are used for deriving tNRI (threshold of neural response imaging) levels are described in US 2015/0032181 A1 and US 2008/0221640A1.

According to the example of FIG. 1, the sound processing subsystem 11 further comprises an electrode migration monitoring unit 54 which may form part of a sound processor unit 56 which also includes the sound processor 24. Typically, the sound processor unit 56 is a BTE (behind-the-ear) unit or a portable speech processor ("PSP") unit which is not worn at ear level but may be worn, for example, at a belt around the patient's body.

According to an alternative embodiment, wherein the CI system is designed as a fully implantable system, the sound processor 24 and the electrode migration monitoring unit 54 may form part of an implantable arrangement.

The electrode migration monitoring unit 54 includes several components, namely a unit 58 for capturing ECAP signals induced at the electrodes 18 of the electrode array 19 in FIG. 2. Monitoring is in response to stimulation of the cochlea by applying auditory nerve stimulation signals to the electrodes 18 and typically is carried out by reverse telemetry (this principle is illustrated in FIG. 4). Other components include, a memory unit 60, an electrode migration detection unit 62 and a unit 64 for outputting an alarm signal in case that electrode migration is detected.

The memory unit 60 is used for storing captured ECAP signals and/or ECAP data derived from captured ECAP signals, such as a neural response threshold value which may be derived, for example, from growth function measurements (see for example US 2015/0032181 A1 and US 2008/0221640 A1).

The electrode migration detection unit 62 is adapted to detect electrode migration relative to the cochlea by comparing presently captured ECAP signals and/or ECAP data derived from such presently captured ECAP signals to previously captured ECAP signals and/or ECAP data derived from previously captured ECAP signals. Such previously captured ECAP signals, or the respectively derived ECAP data, are stored in the memory unit 60 (it could make sense to store both, and in addition measured electrode impedance values; with the baseline values stored it is only necessary to store either the most recent value found to diverge significantly from the baseline or some weighted average of the whole history to allow a comparison to be made with historical and current data). To this end, the electrode migration detection unit 62 may analyze, for example, neural response profiles of the electrode array 19, wherein for each electrode a neural response threshold value is determined, for example by growth function measurements. In this case, a correlation analysis of the neural response profile obtained from previously captured ECAP signals and the neural response profile obtained from the presently captured ECAP signals is conducted in order to detect the occurrence of an electrode-wise shift of the neural response profile, with such shift being indicative of electrode migration.

Figure 5:
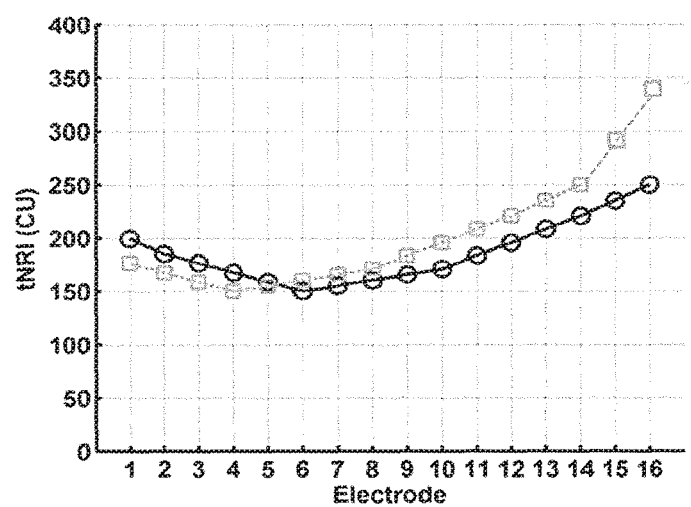
FIG. 5 is an example of an ECAP threshold profile for an electrode array before and after electrode migration.

An example of such comparison is shown in FIG. 5, wherein an example of a neural response profile prior to the occurrence of electrode migration is indicated by circles (the positions are indicative of the determined neural response threshold "tNRI") and wherein the respective neural response profile after the occurrence of electrode migration is indicated by squares. The example of FIG. 5 assumes that due to the electrode migration two basal electrodes have moved out of the cochlea (namely electrodes #15 and #16; electrode #1 indicates the most apical electrode in FIG. 5). It can be seen in FIG. 5 that the migration of electrodes #15 and #16 out of the cochlea results in a shift of the entire neural response profile by two electrodes to the left (i.e. after migration electrode #12 has a neural response similar to that of electrode #14 prior to migration, electrode #11 after migration has a neural response similar to that of electrode #13 prior to migration, etc.).

It is obvious that such shift of the neural response profile only can be detected in case that the profile is not "flat" (in a "flat" profile, all electrodes have approximately the same neural response). However, in such cases the electrode migration monitoring unit 54 may utilize the effect that for those electrodes which have migrated out of the cochlea a significant increase of the neural response threshold is to be expected (such increase can be seen in FIG. 5 for the electrodes #15 and #16). Thus, the electrode migration monitoring unit 54, in addition to detecting electrode-wise shifts of the neural response profile, also may detect electrode migration from an increase of the neural response threshold values of at least one or two of the most basal electrodes above a given threshold increase limit. Such threshold increase is expected only for the most basal electrodes, since only the most basal electrodes may migrate out of the cochlea.

Further, the electrode migration monitoring unit 54 may be adapted to ground at least one of the most basal electrodes in order to determine an effect of such grounding on the ECAP signals of adjacent electrodes. In this case, the ECAP signals obtained during grounding will be compared to the ECAP signals obtained without grounding, and in case that a significant effect, i.e. an effect exceeding a given "grounding effect limit", is observed, it may be decided that electrode migration has occurred. The benefit of such grounding measurements is that one can expect that the current delivered from an electrode which has migrated out of the cochlea would be soaked up by an adjacent electrode before it could produce a neural response. Thus, even slowly or late occurring electrode migration out of the cochlea which does not show a significant effect in standard neural response recording may become detectable by such grounding measurements.

In addition to the neural response analysis, the electrode migration monitoring unit 54 may conduct measurements of the impedance of at least some or all electrodes and store such measured impedance values in the memory unit 60 in order to detect changes in the electrode impedance, with detected changes in electrodes in the impedance being taken into account when deciding whether electrode migration has occurred or not. Preferably, such electrode impedance measurements are conducted each time ECAP measurements are conducted.

In this regard it is to be noted that impedance measurements alone are not a reliable tool for detecting electrode migrations, since changes of electrode impedance may have other reasons than electrode migration, or electrode migration may not result in an electrode impedance change. The latter effect is confirmed by the Dietz (2015) article where, despite sound quality change prompting a further radiologic evaluation, in 25% of cases there was no change in electrode impedances found despite there being electrode array migration. For example, tissue growth around extra-cochlea electrodes may reduce or obscure any impedance change. While a tissue sheath would not be present immediately after implantation, so that impedance changes of the most basal electrodes due to migration may be observable, this may be not be possible in case that electrode migration takes place some weeks or months following implantation, since then a sheath would have developed around the extra-cochlea electrode lead, which would allow the electrode array to move within such fixed sheath without a significant impedance chance being observable.

The capturing of ECAP signals (and the subsequent comparing of the ECAP signals and/or ECAP data to previous measurements) is conducted on a regular basis, for example every day (or every second or third day) when the CI system was switched on.

Once an electrode migration event has been detected by the electrode migration monitoring unit 54, the alarm unit 64 will issue a corresponding alarm message to the patient or to facility which is in charge of the patient (typically a clinic). An alarm message may be presented to the patient by playing an alarm sound or an alarm message via the stimulation subsystem 12 (i.e. the alarm unit 64 causes the sound processor 24 to generate a corresponding auditory nerve stimulation signal to be sent to the stimulation subsystem 12) or by generating an optical alarm signal, such as a particular flashing pattern of an LED 66 (typically, the sound processor unit 56 anyway comprises an LED). An alarm message may be sent to the patient's clinic by using an accessory device 68 which is connected to a communication network, such as the internet or telephone network, with the sound processor unit 56 comprising an interface 70 (which, as in the example of FIG. 1, may be wireless) for data exchange with the accessory device 68.

What is claimed is:

1. A system comprising:
    a unit for capturing ECAP signals induced at electrodes of an electrode array in response to stimulation of a cochlea by applying auditory nerve stimulation signals to the electrodes;
    a memory unit for storing the captured ECAP signals and/or ECAP data derived from the captured ECAP signals;
    an electrode migration detection unit for detecting electrode migration relative to the cochlea by comparing presently captured ECAP signals and/or ECAP data derived from such presently captured ECAP signals to stored previously captured ECAP signals and/or ECAP data derived from such previously captured ECAP signals; and
    a unit for outputting an alarm signal in case that electrode migration is detected by the electrode migration detection unit.

2. The system of claim 1, further comprising a processor adapted to determine from the ECAP signals for each electrode a neural response threshold value in order to obtain a neural response profile of the electrode array as the derived ECAP data.

3. The system of claim 2, wherein the processor is further adapted to conduct a correlation analysis of the neural response profile obtained from the previously captured ECAP signals and the neural response profile obtained from the presently captured ECAP signals in order to detect the occurrence of an electrode-wise shift of the neural response profile indicative of electrode emigration.

4. The system of claim 2, wherein the processor is further adapted to detect the occurrence of electrode migration in case that an increase of the neural response threshold value of at least a most basal electrode of the electrode array exceeding a given threshold increase limit is determined.

5. The system of claim 4, wherein the processor is further adapted to detect the occurrence of electrode migration in case that an increase of the neural response threshold values of at least the two most basal electrodes of the electrode array each exceeding a given threshold increase limit is determined.

6. The system of claim 1, further comprising a processor adapted to ground at least one of one or more most basal electrodes of the electrode array in order to determine an effect of such grounding on the ECAP signals of adjacent electrodes by comparing the ECAP signals obtained with the grounding to the ECAP signals obtained without the grounding, and wherein an increase of the effect of such grounding above a given grounding effect limit is indicative of electrode migration.

7. The system of claim 1, wherein the capturing and comparing are repeated periodically during times when the cochlear implant system is switched on.

8. The system of claim 1, wherein the alarm unit is adapted to generate an auditory nerve stimulation signal corresponding to an alarm message.

9. The system of claim 1, further comprising an LED, and wherein the alarm unit is adapted to control the LED in a manner so as to generate an optical alarm signal.

10. The system of claim 1, further comprising an interface to an accessory device to be connected to a communication network, and wherein the alarm unit is adapted to generate an alarm message to be sent to a clinician via the accessory device and the communication network.

11. The system of claim 1, further comprising a processor adapted to measure the impedance of at least some of the electrodes and to store measured impedance values in the memory unit in order to detect changes in the electrode impedance, wherein detected changes in electrode impedance are taken into account in the electrode migration detecting by the electrode migration detecting unit.

12. The system of claim 11, wherein the processor is adapted to measure an impedance of one or more of the electrodes each time ECAP signals are captured.

13. The system of claim 1, further comprising:
a microphone arrangement for providing an input audio signal;
a sound processor for generating an auditory nerve stimulation signal from the input audio signal; and
an implantable stimulation assembly comprising the electrode array to be implanted into a cochlea of a patient for electrical stimulation of the cochlea according to the auditory neural stimulation signal.

14. The system of claim 13, wherein the sound processor is part of an arrangement which is external to the patient and which is adapted to communicate with the implantable stimulation assembly via a wireless transcutaneous link.

15. The system of claim 13, wherein the sound processor is configured to be external to the patient.

16. The system of claim 13, wherein the sound processor is a BTE unit or a body worn unit.

17. The system of claim 13, wherein the sound processor is configured to be implanted within the patient.

18. The system of claim 1, wherein the capturing and the comparing are repeated on a regular basis.

19. A method comprising:
capturing ECAP signals induced at electrodes of an electrode array in response to stimulation of a cochlea by applying auditory nerve stimulation signals to the electrodes;
storing the captured ECAP signals and/or ECAP data derived from the captured ECAP signals;
detecting electrode migration relative to the cochlea by comparing presently captured ECAP signals and/or ECAP data derived from such presently captured ECAP signals to stored previously captured ECAP signals and/or ECAP data derived from such previously captured ECAP signals; and
outputting an alarm signal in case that electrode migration is detected by the electrode migration detection unit.

20. The method of claim 19, further comprising determining from the ECAP signals for each electrode a neural response threshold value in order to obtain a neural response profile of the electrode array as the derived ECAP data.

* * * * *